US010980490B2

(12) United States Patent
Jang et al.

(10) Patent No.: US 10,980,490 B2
(45) Date of Patent: Apr. 20, 2021

(54) METHOD AND APPARATUS FOR EVALUATING PHYSIOLOGICAL AGING LEVEL

(71) Applicant: SAMSUNG ELECTRONICS CO., LTD., Suwon-si (KR)

(72) Inventors: Dae-Geun Jang, Yongin-si (KR); Sang Joon Kim, Hwaseong-si (KR); JongPal Kim, Seoul (KR); Seungchul Jung, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 748 days.

(21) Appl. No.: 14/989,947

(22) Filed: Jan. 7, 2016

(65) Prior Publication Data

US 2016/0361027 A1 Dec. 15, 2016

(30) Foreign Application Priority Data

Jun. 15, 2015 (KR) .................. 10-2015-0084430

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0205* (2013.01); *A61B 5/02405* (2013.01); *A61B 5/1118* (2013.01); *A61B 5/4857* (2013.01); *A61B 5/7235* (2013.01); *G06F 19/00* (2013.01); *G16H 50/30* (2018.01); *A61B 5/021* (2013.01); *A61B 5/02125* (2013.01)

(58) Field of Classification Search
CPC ... A61B 5/7275; A61B 5/0205; A61B 5/1118; A61B 5/4857; A61B 5/7235; G16H 50/30
See application file for complete search history.

(56) References Cited

U.S. PATENT DOCUMENTS 5,176,133 A 1/1993 Czeisler et al.
6,547,729 B1\* 4/2003 Abbo .................. A61B 5/0002
128/923

(Continued)

FOREIGN PATENT DOCUMENTS

EP 0113200 A1 7/1984
EP 2881035 A1 6/2015
(Continued)

OTHER PUBLICATIONS

Definition of Circadian. Merriam-Webster Dictionary, retrieved on Jun. 11, 2019; Retrieved from Internet: <http://www.merriam-webster.com/dictioanry/circadian> (Year: 2019).*

(Continued)

*Primary Examiner* — Gary Jackson
*Assistant Examiner* — Sebastian X Lukjan
(74) *Attorney, Agent, or Firm* — NSIP Law

(57) ABSTRACT

A method of evaluating a physiological aging level includes calculating a complexity corresponding to a change pattern of a physiological parameter sensed from a user, and determining an aging level indicating a physiological change progress of the user based on the complexity.

32 Claims, 12 Drawing Sheets

(51) Int. Cl.
*A61B 5/11* (2006.01)
*A61B 5/024* (2006.01)
*G16H 50/30* (2018.01)
*A61B 5/021* (2006.01)
*G06F 19/00* (2018.01)

(56) References Cited

U.S. PATENT DOCUMENTS

| | | | |
|---|---|---|---|
| 6,811,536 B2 * | 11/2004 | Sun | A61B 5/022 600/500 |
| 7,344,504 B2 | 3/2008 | Ohhashi et al. | |
| 8,529,447 B2 | 9/2013 | Jain et al. | |
| 8,622,901 B2 | 1/2014 | Jain et al. | |
| 2002/0156392 A1 | 10/2002 | Arai et al. | |
| 2007/0066906 A1 | 3/2007 | Goldberger et al. | |
| 2008/0146890 A1 * | 6/2008 | LeBoeuf | A61B 5/0059 600/300 |
| 2008/0195166 A1 * | 8/2008 | Sun | A61B 5/0478 607/18 |
| 2009/0105560 A1 * | 4/2009 | Solomon | A61B 5/0002 600/301 |
| 2009/0292180 A1 * | 11/2009 | Mirow | G16H 10/20 600/301 |
| 2010/0214559 A1 * | 8/2010 | Brainard | A61N 5/0618 356/213 |
| 2012/0136226 A1 | 5/2012 | Wilke | |
| 2014/0081152 A1 * | 3/2014 | Clinton | A61B 5/7235 600/479 |
| 2014/0088444 A1 | 3/2014 | Saalasti et al. | |
| 2014/0288449 A1 | 9/2014 | Wegerif | |
| 2015/0112208 A1 * | 4/2015 | He | A61B 5/0285 600/479 |

FOREIGN PATENT DOCUMENTS

| | | |
|---|---|---|
| JP | 3017474 B2 | 3/2000 |
| JP | 2002-238867 A | 8/2002 |
| JP | 2010-158267 A | 7/2010 |
| JP | 2012-120206 A | 6/2012 |
| JP | 2014-23825 A | 2/2014 |
| KR | 10-0455289 B1 | 11/2004 |
| KR | 10-0510282 B1 | 8/2005 |
| KR | 10-0768586 B1 | 10/2007 |
| KR | 10-2011-0026729 A | 3/2011 |
| KR | 10-2012-0053481 A | 5/2012 |
| KR | 10-2012-0098365 A | 9/2012 |
| KR | 10-2012-0131898 A | 12/2012 |
| KR | 10-1298838 B1 | 8/2013 |
| KR | 10-2014-0122849 A | 10/2014 |
| WO | WO-2015185706 A1 * 12/2015 ........... A61B 5/4818 |

OTHER PUBLICATIONS

Lipsitz, Lewis A., et al., "Loss of 'Complexity' and Aging: Potential Applications of Fractals and Chaos Theory to Senescence," *JAMA (Journal of the American Medical Association)*, vol. 267, No. 13, Apr. 1, 1992, pp. 1806-1809.

Extended European Search Report dated Nov. 14, 2016 in counterpart European Patent Application No. 16159543.4 (9 pages, in English).

Summons to Attend Oral Proceedings issued on Apr. 2, 2019 in counterpart European Patent Application No. 16159543.4 (9 pages in English).

Japanese Office Action dated Dec. 10, 2019 in counterpart Japanese Application No. 2016-042639 (8 pages in English and 3 pages in Japanese).

* cited by examiner

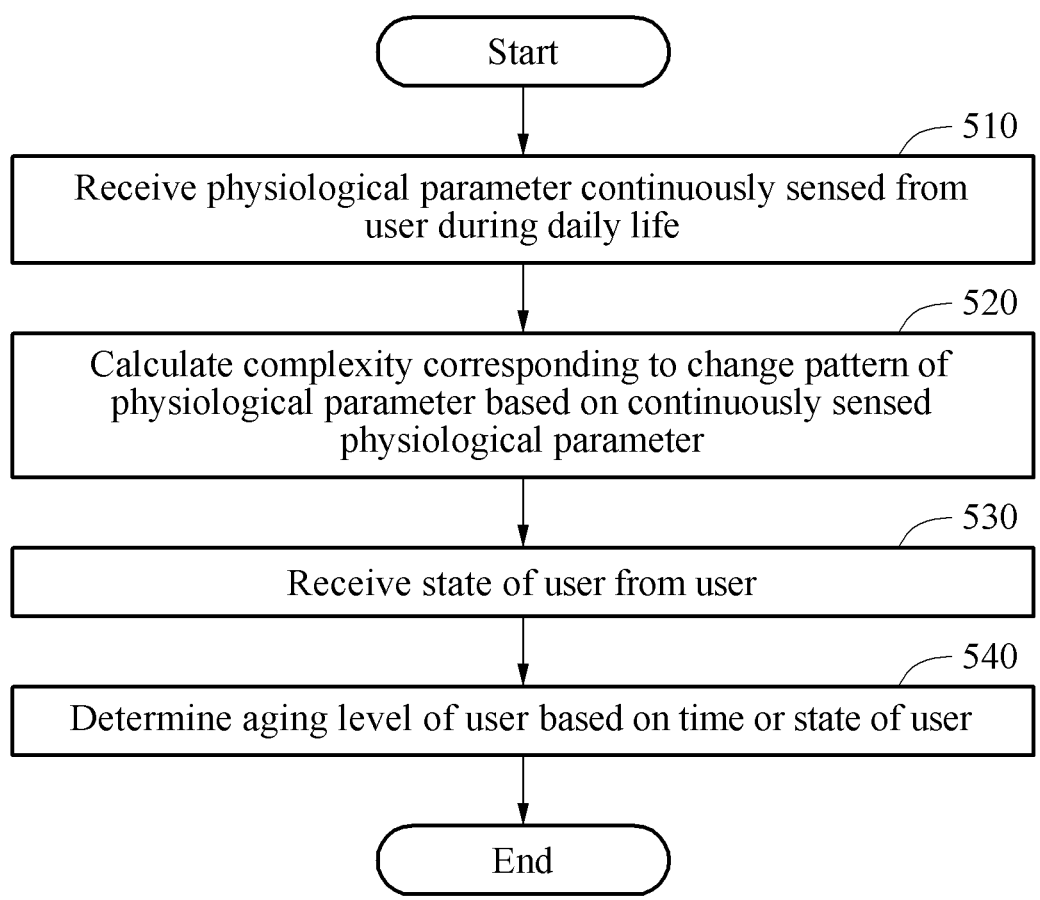

A: Exercise started
B: Exercise ended

METHOD AND APPARATUS FOR EVALUATING PHYSIOLOGICAL AGING LEVEL

CROSS-REFERENCE TO RELATED APPLICATION(S)

This application claims the benefit under 35 USC 119(a) of Korean Patent Application No. 10-2015-0084430 filed on Jun. 15, 2015, in the Korean Intellectual Property Office, the entire disclosure of which is incorporated herein by reference for all purposes.

BACKGROUND

1. Field

The following description relates to a method and an apparatus for evaluating a physiological aging level.

2. Description of Related Art

Aging is a decline phenomenon occurring as humans become older, and is a comprehensive concept including all changes in physiological, biological, social, and psychological characteristics. In general, aging may be diagnosed by discovering a major biomarker of aging and measuring a biological decline phenomenon based on a size, a particle count, and a concentration of the corresponding biomarker. Further, an aging characteristic may be evaluated by measuring a blood circulation state and an elasticity of blood vessels using a photoplethysmogram (PPG) or a second derivative of a photoplethysmogram (SDPTG) measured from a body part and expressing the measured data as a vascular age.

To accurately evaluate the aging characteristic, characteristic parameters, for example, an incisura, a reflected wave, and an initial positive wave, need to be stably collected from the PPG or the SDPTG. However, measuring an accurate pulse waveform in the course of daily life is difficult. In addition, vascular elasticity information measured at a topical body part is used, and thus there is a limitation to an evaluation of an overall aging state of a target.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a method of evaluating a physiological aging level includes calculating a complexity corresponding to a change pattern of a physiological parameter sensed from a user based on the physiological parameter sensed from the user; and determining an aging level indicating a physiological change progress of the user based on the complexity.

The calculating may include either one or both of calculating a variance in the complexity based on the complexity; and calculating a relative ratio of the physiological parameter to the complexity or a relative ratio of a variance in the physiological parameter to the complexity.

The determining may include determining the aging level based on the complexity and either one or both of the variance in the complexity and the relative ratio.

The determining may include determining the aging level by substituting the complexity into an aging function.

The aging function may include at least one coefficient determined using a regression analysis performed based on the complexity and information related to an age of the user.

The calculating may include calculating the complexity of the physiological parameter based on any one or any combination of any two or more of a Poincare plot of the physiological parameter, a fractal dimension of the physiological parameter, a chaotic dynamic parameter of the physiological parameter, and an entropy of the physiological parameter.

The calculating may include calculating a decrease rate of the complexity or an increase rate of the complexity.

The physiological parameter may include any one or any combination of any two or more of a heart rate, a blood pressure, and a pulse transit time (PTT) of the user.

The method may further include receiving a physiological parameter continuously sensed from the user during a daily life of the user; and the calculating may include calculating the complexity based on the physiological parameter continuously sensed from the user.

The determining may include determining a first aging level of the user in a first time interval based on the complexity; and determining a second aging level of the user in a second time interval based on the first aging level.

The determining may include evaluating an aging level of the user based on a reference aging level.

The determining may include determining the aging level of the user based on preset gender-specific and age-specific aging levels.

The determining may include determining the aging level of the user based on a time or a state of the user; and the state of the user may be based on a physical activity of the user.

The method may further include receiving the state of the user from the user.

The method may further including generating information related to a circadian rhythm of the user based on the aging level.

The generating may include generating cumulative information related to the circadian rhythm by accumulating information related to the circadian rhythm generated during a predetermined period.

The method may further including generating information indicating a standard biorhythm of the user based on the cumulative information.

The method may further include generating information for improving a life habit of the user based on the information indicating the standard biorhythm of the user; and providing the information for improving the life habit to the user.

The generating of the information related to the circadian rhythm may include generating information indicating a daily circadian rhythm of the user.

The method may further include calculating a synchronicity between the daily circadian rhythm of the user and the standard biorhythm of the user; evaluating an irregularity in a life pattern of the user based on the synchronicity; and providing feedback on the evaluated irregularity to the user.

The method may further include providing any one or any combination of any two or more of a life habit guidance, an exercise program, and a rest program for the user based on the information related to the circadian rhythm of the user.

In another general aspect, a non-transitory computer-readable storage medium stores instructions to cause a computer to perform the method of claim 1.

In another general aspect, an apparatus for evaluating a physiological aging level includes a sensor configured to sense a physiological parameter from a user; and a processor configured to calculate a complexity corresponding to a change pattern of the physiological parameter based on the physiological parameter sensed from the user, and determine an aging level indicating a physiological change progress of the user based on the complexity.

The processor may be further configured to calculate either one or both of a variance in the complexity and a relative ratio that is a relative ratio of the physiological parameter to the complexity or a relative ratio of the variance in the physiological parameter to the complexity, and determine the aging level based on the complexity and either one or both of the variance in the complexity and the relative ratio.

The sensor may be further configured to continuously sense the physiological parameter from the user during daily life of the user; and the processor may be further configured to calculate the complexity based on the physiological parameter continuously sensed from the user.

The processor may be further configured to determine a first aging level of the user in a first time interval, and determine a second aging level of the user in a second time interval based on the first aging level.

The processor may be further configured to evaluate the aging level of the user relative to an actual age of the user or a target age based on a reference aging level corresponding to the actual age of the user or the target age.

The processor may be further configured to determine the aging level of the user based on a time or a state of the user; and the state of the user may be based on a physical activity of the user.

The apparatus may further include a user interface (UI) configured to receive the state of the user from the user.

The processor may be further configured to generate information related to a circadian rhythm of the user based on the aging level.

The processor may be further configured to generate cumulative information by accumulating information related to the circadian rhythm generated during a predetermined period, and generate information indicating a standard biorhythm of the user based on the cumulative information.

In another general aspect, an apparatus for evaluating an aging characteristic includes a sensor configured to sense a physiological parameter from a user; and a processor configured to calculate a complexity corresponding to a change pattern of the physiological parameter based on the physiological parameter sensed from the user, and determine an aging characteristic of the user based on the complexity.

The processor may be further configured to compare the aging characteristic of the user to a reference aging characteristic, and evaluate the aging characteristic of the user based on a result of the comparing.

The processor may be further configured to calculate a difference between the aging characteristic of the user and a reference aging characteristic, accumulate the difference over a period of time, and evaluate the aging characteristic of the user based on the accumulated difference.

The aging characteristic of the user may be an aging level of the user that changes as a level of physical activity of the user changes and represents a physiological change progress of the user due to aging of the user; the reference aging characteristic may be a reference aging level corresponding to an actual age of the user or a target age; and the processor may be further configured to evaluate the aging level of the user as being greater than the reference aging level in response to the accumulated difference being positive, and as being less than the reference aging level in response to the accumulated difference being negative.

Other features and aspects will be apparent from the following detailed description, the drawings, and the claims.

BRIEF DESCRIPTION OF THE DRAWINGS

FIG. 5 is a flowchart illustrating another example of a method of evaluating a physiological aging level.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

The terminology used herein is for the purpose of describing particular examples only, and is not to limit the disclosure. As used herein, the singular forms "a", "an", and "the"

are intended to include the plural forms as well, unless the context clearly indicates otherwise. As used herein, the terms "include," "comprise," and "have" specify the presence of stated features, numbers, operations, elements, components, and combinations thereof, but do not preclude the presence or addition of one or more other features, numbers, operations, elements, components, and combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

Figure 1A:
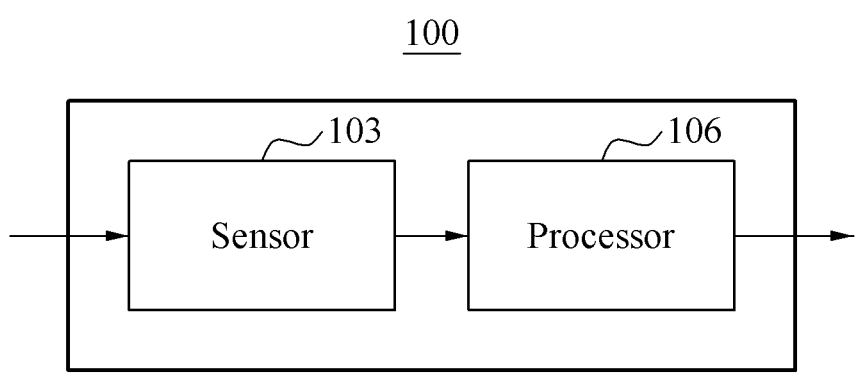
FIG. 1A is a block diagram illustrating an example of an apparatus for evaluating a physiological aging level.
Figure 1B:
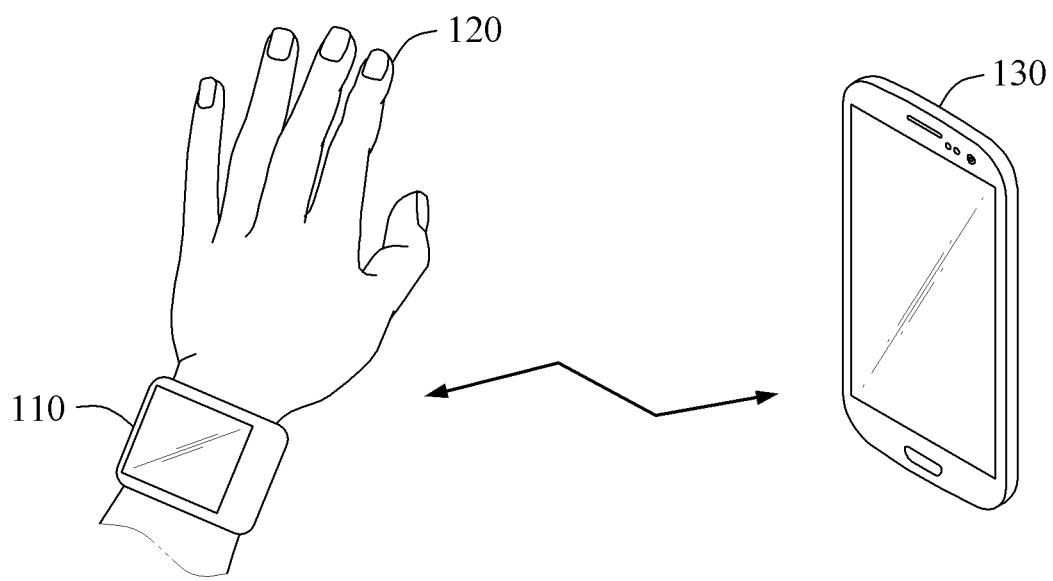
FIG. 1B is a diagram illustrating an example of devices in which an apparatus for evaluating a physiological aging level is embedded.

FIG. 1A is a block diagram illustrating an example of an apparatus for evaluating a physiological aging level, and FIG. 1B is a diagram illustrating an example of devices in which an apparatus for evaluating a physiological aging level is embedded.

Referring to FIG. 1A, an apparatus 100 for evaluating a physiological aging level, hereinafter referred to as the evaluation apparatus 100, includes a sensor 103 and a processor 106.

The sensor 103 senses a physiological parameter from a user. For example, the physiological parameter may be a heart rate, a blood pressure, or a pulse transit time (PTT) of the user. The sensor 103 may include a plurality of sensing elements sensing a plurality of physiological parameters.

The sensor 103 may continuously sense the physiological parameter from the user during daily life, such as sleeping, eating, walking, exercising, working, and getting to work, for example. Alternatively, the sensor 103 may regularly sense the physiological parameter at a predetermined time interval, for example, at an interval of 10 minutes, for a predetermined time period, for example, for 15 seconds or 30 seconds.

The processor 106 calculates a complexity of the physiological parameter based on the physiological parameter. The complexity of the physiological parameter corresponds to a change pattern of the physiological parameter. For example, in a case of a young subject, a change pattern of a heart rate will be much more complicated and varied even though the young subject has the same average heart rate as an old subject. A complexity of a physiological parameter will be described with reference to FIGS. 4A and 4B. The processor 106 calculates the complexity based on the physiological parameter sensed continuously from the user or the physiological parameter sensed regularly at the predetermined time interval.

The processor 106 determines an aging level based on the complexity. The "aging level" differs from a biological age or a physiological age of the user verified at a predetermined point in time. The aging level corresponds to, for example, an aging index, or an aging characteristic. The aging level represents a physiological change progress of the user, for example, that aging is being accelerated or that aging is being suppressed.

In addition to the complexity, the processor 106 calculates either one or both of a variance in the complexity and a relative ratio of the physiological parameter to the complexity. The processor 106 determines the aging level based on any one or any combination of any two or more of the complexity, the variance in the complexity, and the relative ratio. The processor 106 calculates either one or both of the variance in the complexity and the relative ratio of the physiological parameter to the complexity based on the physiological parameter sensed continuously from the user or the physiological parameter sensed regularly at the predetermined time interval.

In one example, the processor 106 determines the aging level based on the complexity of the physiological parameter, the variance in the complexity, the relative ratio, and a variability of the physiological parameter. The expression "variability of the physiological parameter" refers to a periodic change in a physiological parameter occurring over time due to a change in a body or an external environment. For example, the variability may be calculated based on a mean of the physiological parameter, a variance, a standard deviation, a skewness, a kurtosis, a spectrum power in a predetermined frequency band, or other characteristics of the physiological parameter.

Figure 6:
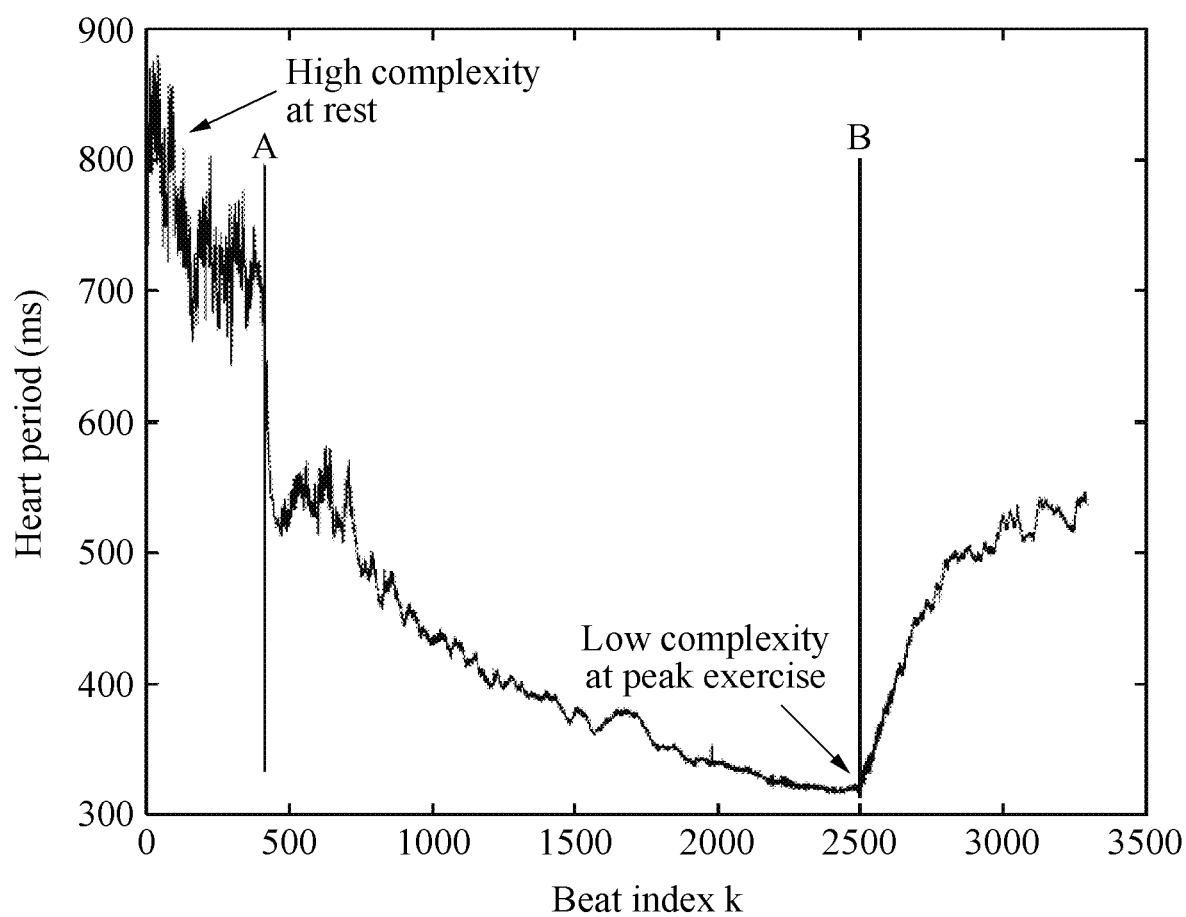
FIG. 6 is a graph illustrating an example of an aging level differing for each state of a user in a method of evaluating a physiological aging level.

The evaluation apparatus 100 may further include a user interface (UI) (not shown) configured to receive a state of the user. The state of the user is determined based on a physical activity of the user, such as eating, sleeping, watching TV, working, resting, exercising at high intensity, exercising at moderate intensity, and exercising at low intensity, for example. The state of the user is divided into an exercise state, a sleeping state, and a sedentary state. The state of the user is input from the user through the UI of the evaluation apparatus 100. The UI is displayed on a display of a wearable device or a mobile device in which the evaluation apparatus 100 is embedded. The aging level of the user differs for each state of the user, for example, as shown in FIG. 6. The processor 106 determines the aging level of the user based on the state of the user.

The processor 106 determines the aging level of the user based on a time. The processor 106 determines a first aging level of the user in a first time interval, and determines a second aging level of the user in a second time interval based on the first aging level. For example, when a biological age, in detail, an actual age of the user is 31, the processor 106 evaluates a physiological aging level corresponding to the current age of 31 of the user based on a physiological aging level evaluated during a time period of the user at the age of 30. The processor 106 evaluates a physiological aging level of the user today based on a physiological aging level of the user evaluated yesterday, or evaluates a physiological aging level of the user in the afternoon based on a physiological aging level of the user evaluated in the morning.

The processor 106 evaluates the aging level of the user relative to an actual age of the user based on a reference aging level corresponding to the actual age of the user. A method of evaluating an aging level of a user based on a reference aging level using the processor 106 will be described with reference to FIG. 7.

The processor 106 generates information related to a circadian rhythm of the user based on the evaluated aging level. The circadian rhythm refers to a phenomenon that a biochemical, physiological, or ethological process has a cycle of about 24 hours in a living thing on the earth. In particular, according to a circadian rhythm of each user, a body temperature, a blood pressure, a hormone secretion, and a cell division in a human body may change in a cycle of one day. The information related to the circadian rhythm of the user may be construed as including a circadian rhythm of the user biochemically and/or physiologically verified, for example, the body temperature, the blood pressure, the hormone secretion, and the cell division, and information indicating the circadian rhythm of the user, for example, a graph or data representing the circadian rhythm. A method of generating information related to a circadian rhythm using the evaluation apparatus 100 will be described with reference to FIG. 9.

The processor 106 generates cumulative information related to the circadian rhythm by accumulating information related to the circadian rhythm generated during a predetermined time period, for example, a day, a week, and a month. The processor 106 generates information indicating a standard biorhythm of the user based on the cumulative information. The information indicating the standard biorhythm of the user may be, for example, a graph or a list representing the standard biorhythm of the user.

Referring to FIG. 1B, a wearable device 110 and a mobile device 130 in which the evaluation apparatus 100 is embedded are illustrated.

An operation of a case in which the evaluation apparatus 100 is embedded in the wearable device 110 will be described. For example, the wearable device 110 may be a wrist-worn device provided in a shape of a watch or a bracelet, or may be provided in a shape of a necklace or various other shapes. When a user 120 wears the wearable device 110, the evaluation apparatus 100 calculates a complexity of a physiological parameter based on the physiological parameter, such as a heart rate, a blood pressure, and a PTT, measured from a body part of the user 120. The evaluation apparatus 100 determines an aging level indicating a physiological change progress of the user 120 based on the complexity.

The wearable device 110 including the evaluation apparatus 100 interoperates with the mobile device 130, and the wearable device 110 and the mobile device 130 share data. For example, the heart rate, the blood pressure, and the PTT measured from the user 120, the complexity of the physiological parameter, and the aging level of the user are transmitted to the mobile device 130. The mobile device 130 transmits information related to age-specific and gender-specific physiological aging levels to the evaluation apparatus 100.

In another example, the processor 106 of the evaluation apparatus 100 is embedded in the mobile device 130, and the sensor 103 of the evaluation apparatus 100 is embedded in the wearable device 110. The wearable device 110 is worn on a body part, for example, a wrist, of the user 120 to measure the heart rate, the blood pressure, and the PTT of the user 120 from the wrist. The wearable device 110 amplifies and filters the heart rate, the blood pressure, and the PTT measured from the user 120. The wearable device 110 transmits the heart rate, the blood pressure, and the PTT to the mobile device 130.

The evaluation apparatus 100 included in the mobile device 130 calculates a complexity corresponding to a change pattern of the physiological parameter of the user 120 based on the heart rate, the blood pressure, and the PTT received from the wearable device 110. The mobile device 130 determines an aging level indicating a physiological change progress of the user 120 based on the complexity. A detailed configuration of an evaluation apparatus including a sensor and a processor being separated from each other as described above will be described with reference to FIG. 2.

Figure 2:
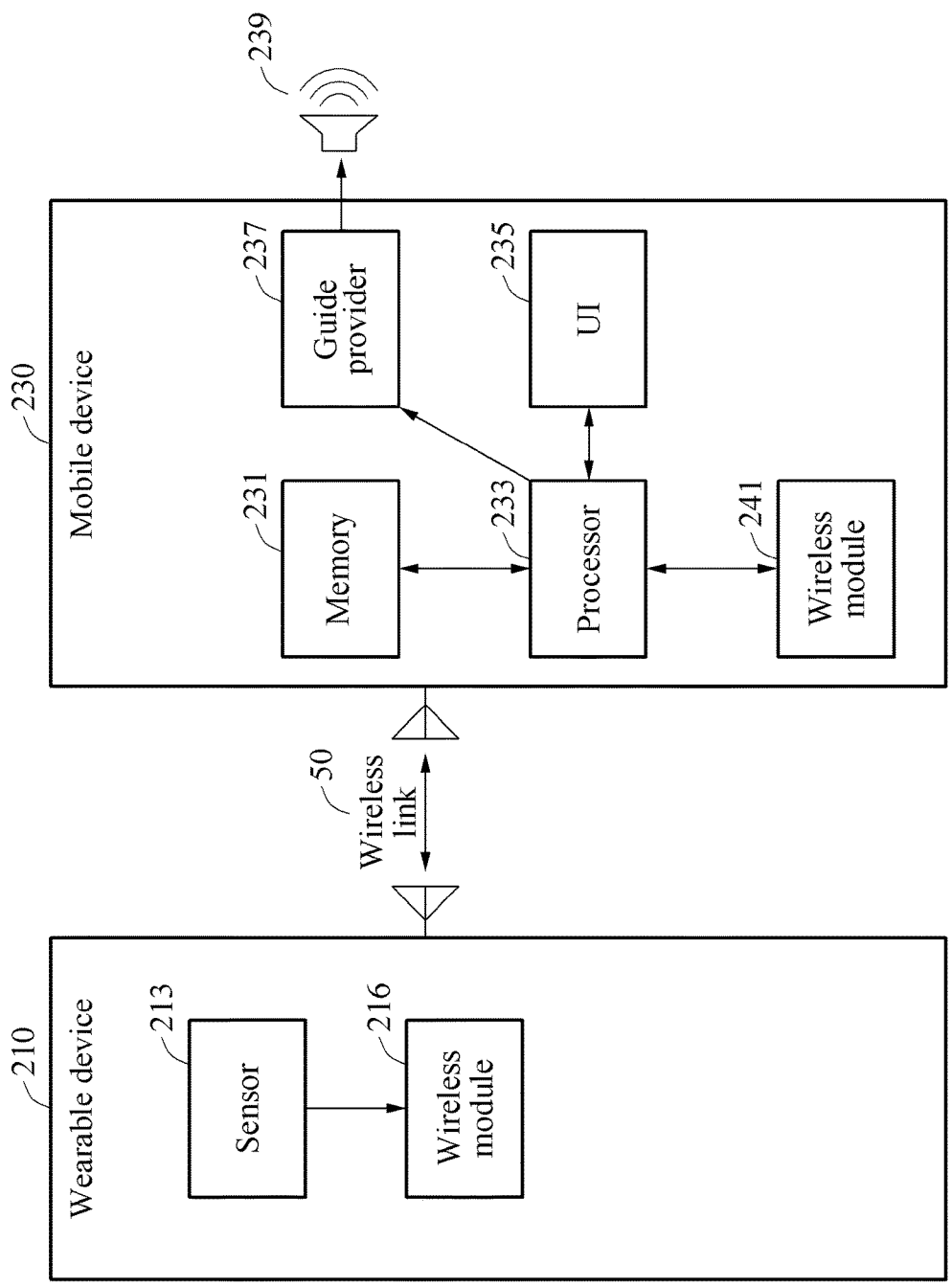
FIG. 2 is a block diagram illustrating another example of an apparatus for evaluating a physiological aging level.

FIG. 2 is a block diagram illustrating another example of an apparatus for evaluating a physiological aging level.

Referring to FIG. 2, a sensor 213 of an evaluation apparatus is included in a wearable device 210, and a processor 233 of the evaluation apparatus is included in a mobile device 230.

In this example, the wearable device 210 and the mobile device 230 are connected to each other via a wireless link 50.

The wearable device 210 and the mobile device 230 may include wireless Internet interfaces, such as a wireless local area network (WLAN) interface, a Wi-Fi interface, a digital living network alliance (DLNA interface), a wireless broadband (WiBro) interface, a world interoperability for microwave access (WiMAX) interface, and a high-speed downlink packet access (HSDPA) interface, for example, and short-range communication interfaces, such as a Bluetooth interface, a radio frequency identification (RFID) interface, an infrared data association (IrDA) interface, a ultra wideband (UWB) interface, a ZigBee interface, and a near field communication (NFC) interface, for example.

The wearable device 210 includes the sensor 213 configured to measure various physiological parameters, for example, a heart rate, a blood pressure, and a PTT. A single sensor 213 or a plurality of sensors 213 may be provided. For example, the sensor 213 may include a photoplethysmogram (PPG) sensor and an ultrasonic blood flow sensor.

The sensor 213 measures a physiological parameter by sensing a potential signal or other parameter of a body part at which a heartbeat or a blood flow of a user may be measured. For example, the sensor 213 measures various physiological parameters of the user from a neck, a chest, a fingertip, a wrist, or a forearm. The sensor 213 continuously senses the physiological parameter from the user during daily life, or regularly senses the physiological parameter at a predetermined time interval.

The physiological parameter measured during the daily life of the user or at a predetermined time interval through the wearable device 210 is transmitted to the mobile device 230 through a wireless module 216 including a wireless Internet interface and/or a short-range communication interface.

The wearable device 210 monitors an aging level of the user in real time. Information about the aging level of the user is transmitted to the mobile device 230 through Bluetooth, Wi-Fi, ZigBee, or a customized communication channel to which a security function is applied.

The mobile device 230 may be implemented as a tablet computer, a smart phone, or a personal digital assistant (PDA), for example. The mobile device 230 may be network equipment such as a server. The mobile device 230 may be a single server computer or a system similar thereto, or at least one server bank or server cloud distributed at different geographical locations.

The mobile device 230 may receive various physiological parameters in addition to the heart rate and the blood pressure through the wearable device 210 or another measurement device (not shown). A state of the user during daily life is input by the user through the wearable device 210 or the mobile device 230.

The mobile device 230 includes a memory 231, the processor 233, a UI 235, a guide provider 237, and a wireless module 241.

The memory 231 includes a database containing information related to physiological aging levels of general users specific to different ages and genders. The memory 231 accumulates and stores aging levels evaluated in real time with respect to a specific user. The memory 231 stores information related to a circadian rhythm of the user, which is generated based on the aging level, and information indicating a standard biorhythm.

The processor 233 determines an aging level indicating a physiological change progress of the user based on the physiological parameter received from the wearable device 210. Hereinafter, the descriptions of the processor 106 of FIG. 1A are also applicable to the processor 233 since an operation of the processor 233 is the same as that of the processor 106.

The UI 235 receives the state of the user from the user. The state of the user is divided into an exercise state, a sleeping state, and a sedentary state. The state of the user is input into the mobile device 230 through the UI 235.

Further, the UI 235 displays a plurality of icons on a touch display (not shown) of the mobile device 230 to receive the state of the user. For example, the user may input the state of the user by selecting one icon corresponding to a physical activity of the user from the icons displayed on the touch display, or selecting one of sentences displayed on the touch display. The touch display may be replaced by a flexible display.

The guide provider 237 provides, to the user, a message guiding the user to input the state of the user through visual or audio guide. For example, the guiding message includes content saying "Please select your current activity" or "Please select sleeping mode before sleep". The guide provider 237 displays, on a screen, the message guiding the user to input the state of the user through the touch display, or provides an alarm guiding the user to input the state of the user.

The guide provider 237 may output the guiding message to a speaker 239. The speaker 239 provides the audio guide including the message guiding the user to input the state of the from the guiding message output from the guide provider 237.

The state of the user input in response to the audio guide is transferred to the processor 233 through the UI 235 or a microphone (not shown).

The wireless module 241 receives, through a wireless Internet interface and/or a short-range communication interface, information including the physiological parameter transmitted from the wireless module 216 of the wearable device 210.

Figure 3:
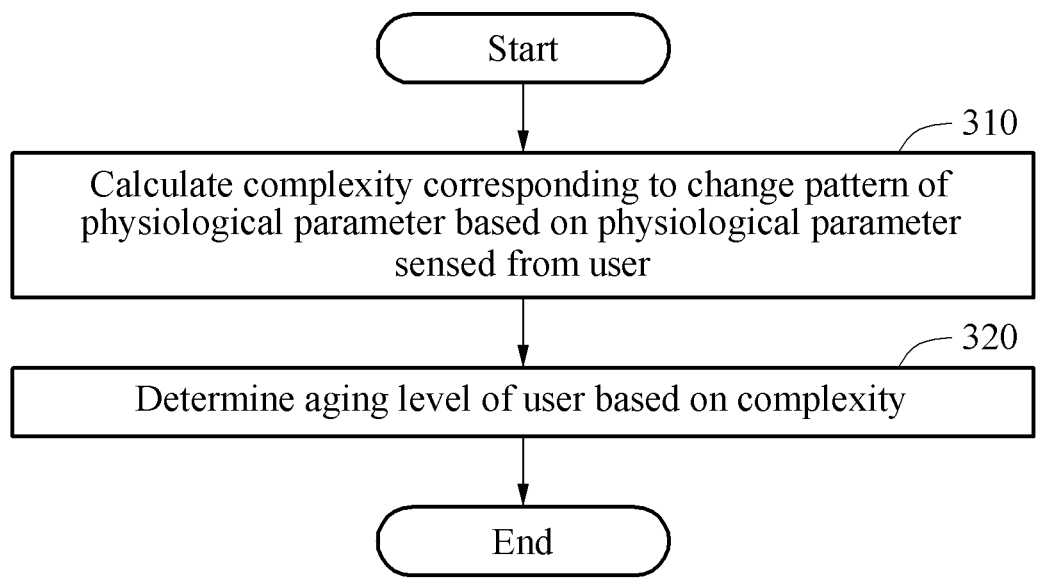
FIG. 3 is a flowchart illustrating an example of a method of evaluating a physiological aging level.

FIG. 3 is a flowchart illustrating an example of a method of evaluating a physiological aging level.

Referring to FIG. 3, an evaluation apparatus calculates a complexity corresponding to a change pattern of a physiological parameter based on the physiological parameter sensed from a user in operation 310. In this example, the physiological parameter includes, for example, a heart rate, a blood pressure, and a PTT.

The evaluation apparatus calculates the complexity based on the physiological parameter continuously sensed from the user during daily life, or based on the physiological parameter sensed regularly at a predetermined time interval. The evaluation apparatus calculates a complexity of the physiological parameter, a variance in the complexity during a predetermined time period, and a relative ratio of the physiological parameter to the complexity or a relative ratio of the variance in the physiological parameter to the complexity.

The evaluation apparatus calculates a decrease rate or an increase rate of the complexity. A complexity of a physiological parameter will be described with reference to FIG. 4.

The evaluation apparatus calculates the complexity of the physiological parameter based on, for example, a Poincare plot of the physiological parameter, a fractal dimension of the physiological parameter, a chaotic dynamic a parameter of the physiological parameter, or an entropy of the physiological parameter.

The fractal dimension may be, for example, a box counting dimension, a correlation dimension, a dimension spectrum (DimSec), a Katz's fractal dimension, or a Higuchi's fractal dimension. The chaotic dynamic parameter may be a Lyapunov exponent, a Hurst exponent, or a scaling exponent. The Lyapunov exponent is a parameter quantifying a dynamical characteristic of information on a phase trajectory, in detail, a separation of two close points, for example, two close states, on the phase trajectory over time after the phase trajectory is implemented from a time series.

The entropy may be, for example, a Shannon entropy (ShannEnt), a Renyi entropy (RenyiEnt), an approximate entropy (ApEn), a sample entropy (SampEnt), or a Kolmogorov-Sinai entropy (K). The ApEn is used to quantify a variance in an unpredictability and regularity of time series data.

The evaluation apparatus determines an aging level indicating a physiological change progress of the user based on the complexity in operation 320. The evaluation apparatus determines the aging level based on any one or any combination of any two or more of the complexity of the physiological parameter, the variance in the complexity, and the relative ratio. In one example, the evaluation apparatus determines the aging level based on a variability of the physiological parameter in addition to any one or any combination of any two or more of the complexity of the physiological parameter, the variance in the complexity, and the relative ratio.

The evaluation apparatus determines the aging level, for example, by substituting the complexity into an aging function. For example, the aging function is a linear or non-linear equation. At least one coefficient of the aging function is determined using a regression analysis performed based on the complexity and information related to an age of the user. The information related to the age of the user includes, for example, an actual age of the user, physiological parameters of a plurality of users at an age corresponding to the actual age of the user, and an average aging level determined based on the physiological parameters of the plurality of users.

For the regression analysis, a machine learning technique, such as a neural network or a support vector machine (SVM), may be used. In another example, a feature vector is generated from the complexity, the variance in the complexity, and the relative ratio. In this example, coefficients of the aging function are determined based on a regression analysis performed based on the feature vector and the information related to the age of the user.

Figure 4A:
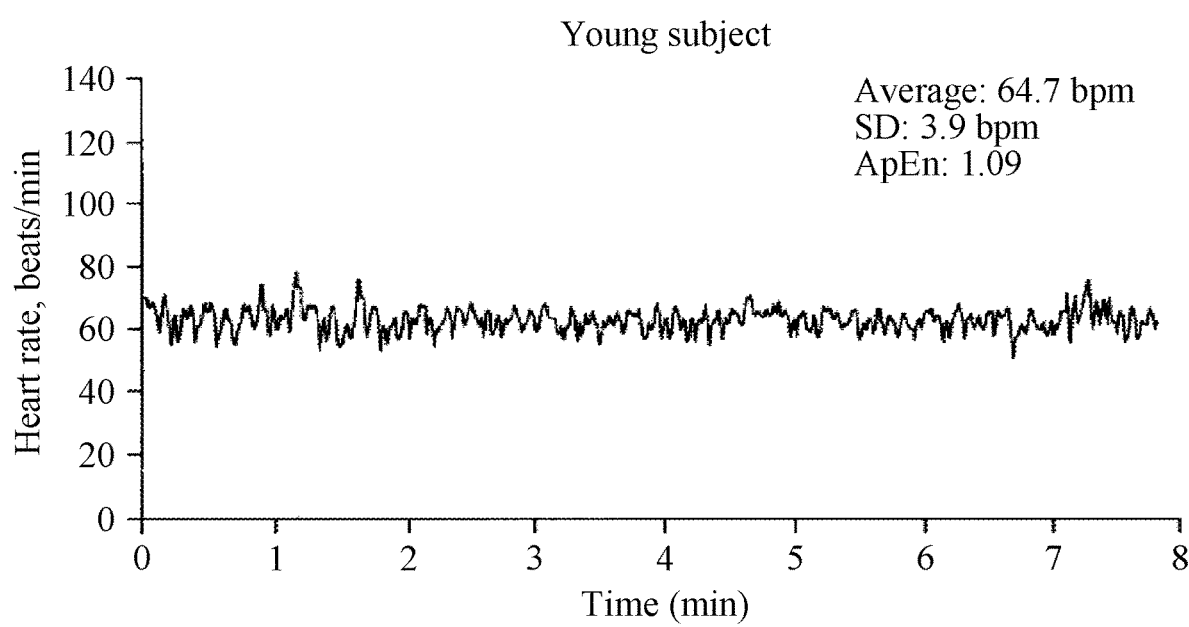
FIG. 4A is a graph illustrating an example of a heart rate of a young subject in its twenties.
Figure 4B:
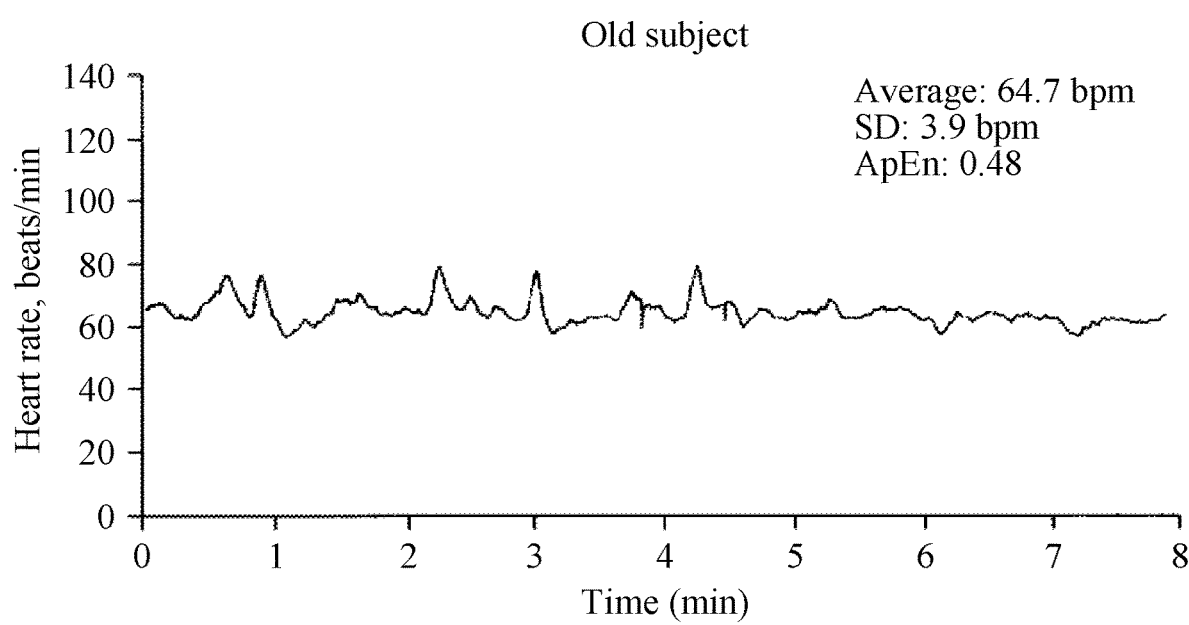
FIG. 4B is a graph illustrating an example of a heart rate of an old subject in its seventies.

FIGS. 4A and 4B are diagrams illustrating a principle of a method of evaluating a physiological aging level.

Referring to FIGS. 4A and 4B, graphs representing complexities of physiological parameters corresponding to different age groups are illustrated. In detail, FIG. 4A is a graph representing a heart rate of a young subject in its twenties, and FIG. 4B is a graph representing a heart rate of an old subject in its seventies.

In both FIGS. 4A and 4B, average heart rates are 64.7 beats per minute (bpm), and standard deviations (SDs) are 3.9 bpm. Thus, the graphs of FIGS. 4A and 4B, it can be seen that the average heart rates and the SDs of the heart rates of the young subject in its twenties and the old subject in its seventies are the same.

However, it can also be seen from FIGS. 4A and 4B that a complexity expressed as an entropy ApEn dramatically decreases from 1.09 in FIG. 4A to 0.48 in FIG. 4B. The complexity may be construed as indicating whether a change pattern of a physiological parameter is complex or simple in a predetermined interval. From the graphs of FIGS. 4A and 4B, it can readily be seen that the complexity of the physiological parameter decreases as the age of the subject increases.

As learned from the graphs of FIGS. 4A and 4B, aging may be defined as a progressive loss of a complexity in a physiological system. In a physiological function, the progressive loss of the complexity may result from, for example, a reduction in a number of dendrites divided from a neurodendrite, an intensiveness of damage, a reduction in a complexity of a heartbeat, a reduction in a complexity of a blood pressure fluctuation, a reduction in a frequency range of electroencephalogram (EEG)-evoked potentials, a reduction in an audible frequency range of hearing, for example, a loss of a high frequency component, a loss or damage to functional components, and a changed non-linear coupling between functional components.

The evaluation apparatus determines the aging level of the user during daily life based on a complexity of a physiological parameter, a variance in the complexity, a relative ratio of a physiological parameter to the complexity, decrease rates thereof, and increase rates thereof, in view of the aforementioned progressive loss of the complexity. Further, the evaluation apparatus immediately provides aging levels corresponding to various physical activities of the user by determining an aging level of the user based on a time and a situation. As described above, the "aging level" is not a biological age of the user that is simply verified at a predetermined point in time, but is construed as indicating a state in which aging is in progress in a body of the user.

FIG. 5 is a flowchart illustrating an example of another method of evaluating a physiological aging level.

Referring to FIG. 5, an evaluation apparatus receives a physiological parameter continuously sensed from a user during daily life in operation 510. The evaluation apparatus calculates a complexity corresponding to a change pattern of the physiological parameter based on the continuously sensed physiological parameter in operation 520.

The evaluation apparatus receives a state of the user from the user through a UI in operation 530. As described above, the state of the user is determined based on a physical activity of the user, such as eating, sleeping, watching TV, working, resting, exercising at high intensity, exercising at moderate intensity, and exercising at low intensity, for example. The state of the users is input by the user through the UI.

The evaluation apparatus determines an aging level of the user based on a time or the state of the user in operation 540. A method of determining an aging level of a user based on a state of the user using the evaluation apparatus will be described with reference to FIG. 6. Further, a method of determining an aging level of a user based on a time will be described with reference to FIG. 7.

FIG. 6 is a graph illustrating an example of an aging level differing for each state of a user in a method of evaluating a physiological aging level.

Referring to FIG. 6, a graph representing a complexity of a physiological parameter in a rest state and an exercise state is illustrated. In the graph of FIG. 6, an axis X denotes a time expressed as a beat index k, which represents a number of heartbeats, and an axis Y denotes a heart period. The heart period is obtained by calculating 1/heart rate. Thus, the heart period decreases as the heart rate increases. In FIG. 6, a point A denotes an instant at which the state changes from the rest state to the exercise state, and a point B denotes an instant at which the state changes from the exercise state to a recovery state, for example, the rest state. In this example, the exercise state refers to an exercise state in an environment in which an exercise intensity progressively increases. Thus, the point B indicates an instant at which an exercise is performed at a highest intensity.

As can be seen from the graph of FIG. 6, a complexity of a heart rate in an interval between a rest state and the point A at which an exercise is initiated, in detail, in a stable state, is much higher than a complexity of a heart rate in an exercise state from the point A at which the exercise is initiated to the peak intensity point B.

The evaluation apparatus evaluates, as being low, the aging level of the stable state, for example, the rest state in which the complexity of the heart rate is high, and evaluates, as being high, the aging level of the exercise state in which the complexity of the heart rate is low. The aging level is evaluated as being high in the exercise state because aging of a human body is accelerated by an occurrence of active oxygen during an exercise. In detail, the exercise itself is an activity that accelerates aging. However, the complexity of the physiological parameter increases in the stable state after the exercise. Thus, the overall complexity of the physiological parameter increases and the overall aging level decreases when compared to the stable state before an exercise is performed.

The evaluation apparatus determines the aging level of the user based on the state of the user by sensing the physiological parameter with respect to each of the physical activities of the user during daily life, such as working, exercising, sleeping, and eating as described above, and calculating the complexity of the physiological parameter.

The aging level of the user is represented in level units from 1 to 10 that indicate an aging suppression or aging acceleration level, for example. The aging level of the user is expressed, for example, as a state in which aging is suppressed or accelerated when compared to a reference state of the user.

Figure 7:
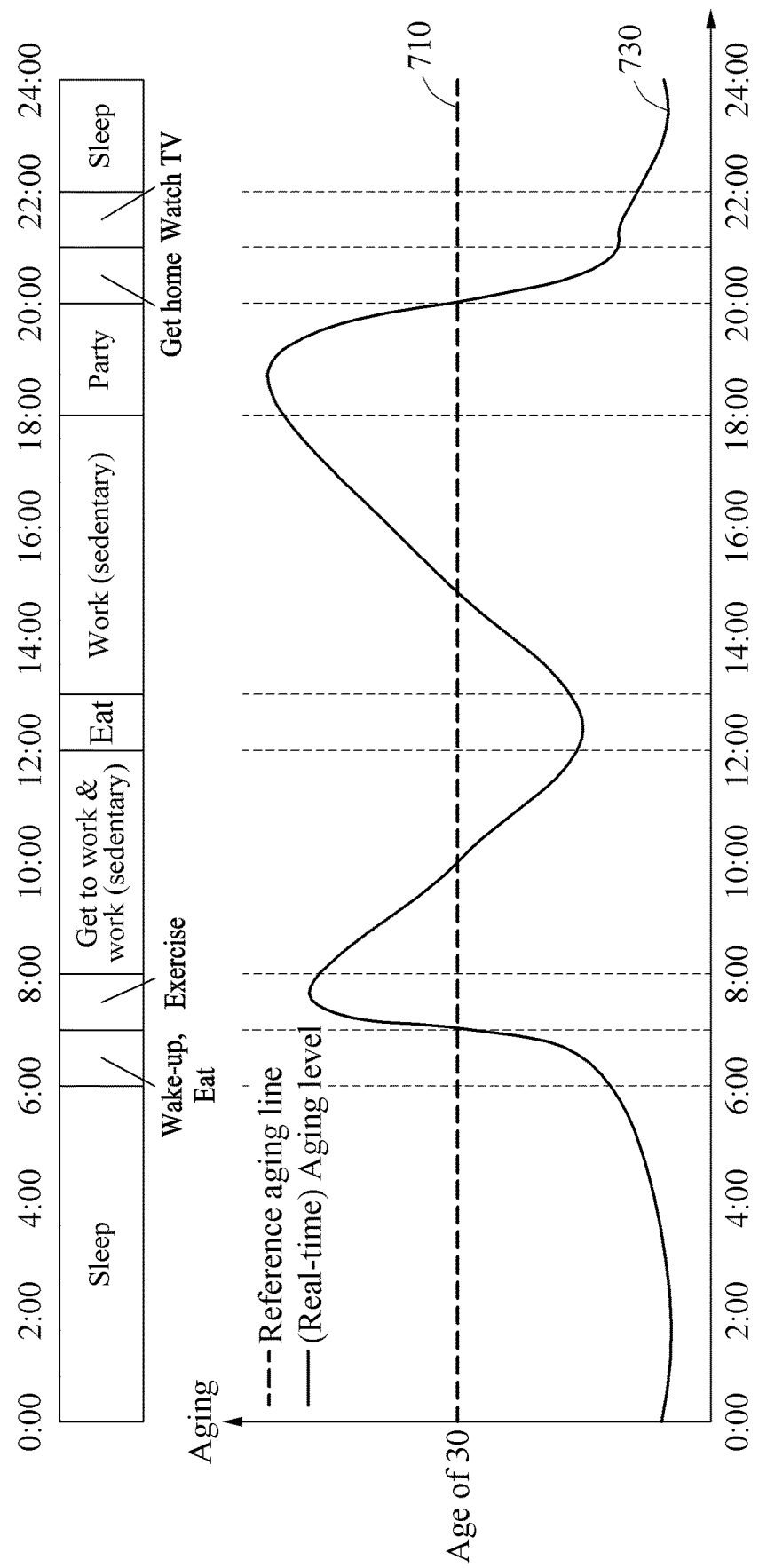
FIG. 7 is a diagram illustrating an example of a method of evaluating an aging level of a user based on a reference aging level.

FIG. 7 is a diagram illustrating an example of a method of evaluating an aging level of a user based on a reference aging level.

Referring to FIG. 7, a graph illustrating an aging level 730 of a user evaluated in real time based on a physiological parameter continuously sensed from the user during daily life is illustrated.

An evaluation apparatus determines the aging level 730 of the user by calculating a complexity of the physiological parameter sensed from the user during daily life. The evaluation apparatus evaluates the aging level 730 of the user based on a reference aging level 710 represented by a reference aging line in the graph. The reference aging level 710 is a reference value to be compared to the aging level 730 of the user. For example, the reference aging level 710 is input directly from the user, set based on an actual age of the user, or preset to be a predetermined target age. The evaluation apparatus evaluates the aging level 730 of the user relative to the actual age of the user based on the reference aging level 710 corresponding to the actual age of the user.

For example, when the actual age of the user is 30, the evaluation apparatus sets an age of 30 corresponding to the actual age of the user as the reference aging level 710. In this example, the reference aging level 710 may be an average value of an aging level during a time period corresponding to the age of 30 of the user. The reference aging level 710 may also be an average aging level of ordinary people at age of 30 pre-stored in a database.

The evaluation apparatus calculates the complexity of the physiological parameter continuously sensed from the user for a day, for example, for 24 hours on June 1st, compares the aging level 730 of the user determined based on the complexity to the reference aging level 710, and calculates a difference between the aging level 730 and the reference aging level 710. When a cumulative value of differences between the aging level 730 of June 1st, and the reference aging level 710 is a positive (+) value, the evaluation apparatus evaluates that the user performed an activity increasing an aging level, for example, an activity accelerating aging, during the day of June 1st. When the cumulative value is a positive value, this indicates that a cumulative quantity of the aging level 730 of June 1st above the reference aging level 710 of FIG. 7 is greater than a cumulative quantity of the aging level 730 below the reference aging level 710.

When the cumulative value of the differences between the aging level 730 of the user and the reference aging level 710 is a negative (−) value, the evaluation apparatus evaluates that the user performed an activity decreasing an aging level, for example, an activity suppressing aging, during the day of June 1st.

The evaluation apparatus provides a feedback on a result of evaluating the aging level to the user. The feedback on the result of evaluating the aging level may be provided to the user in various forms, for example, a message or icon provided through a display, or a voice message. In this example, the message provided through the display may include such as, for example, "your activity of June 1st decreased your aging level," or "you got younger than the age of 30."

In one example, the evaluation apparatus receives a random age desired by the user as a reference aging level, and evaluates the aging level of the user relative to the reference aging level.

In another example, the evaluation apparatus determines a first aging level of the user in a first time interval based on the complexity, and determines a second aging level of the user in a second time interval based on the first aging level. For example, the evaluation apparatus determines an aging level of the user for the second week of June based on an aging level of the user evaluated in April. In another example, the evaluation apparatus determines an aging level of the user in a time interval in the afternoon, for example, in a time interval from six to eleven in the evening, based on an aging level of the user evaluated in a time interval in the morning, for example, in a time interval from six in the morning to noon.

In this example, the evaluation apparatus calculates a difference between the second aging level and the first aging level. When a cumulative value of differences is a positive (+) value, the evaluation apparatus evaluates that the user performed an activity increasing an aging level, for example, an activity accelerating aging, in the second time interval when compared to the first time interval.

In another example, the evaluation apparatus determines the aging level of the user based on a preset gender-specific and age-specific aging level. The gender-specific and age-specific aging level is determined based on a complexity calculated based on physiological parameters of various users of different genders and different ages. The gender-specific and age-specific aging level is pre-stored in a database, for example, in a table or list. The evaluation apparatus determines the aging level by setting the preset gender-specific and age-specific aging level corresponding to a gender, for example, male, and an age, for example, of 35, of the user as the reference aging level, and comparing the aging level of the user to the reference aging level.

Figure 8:
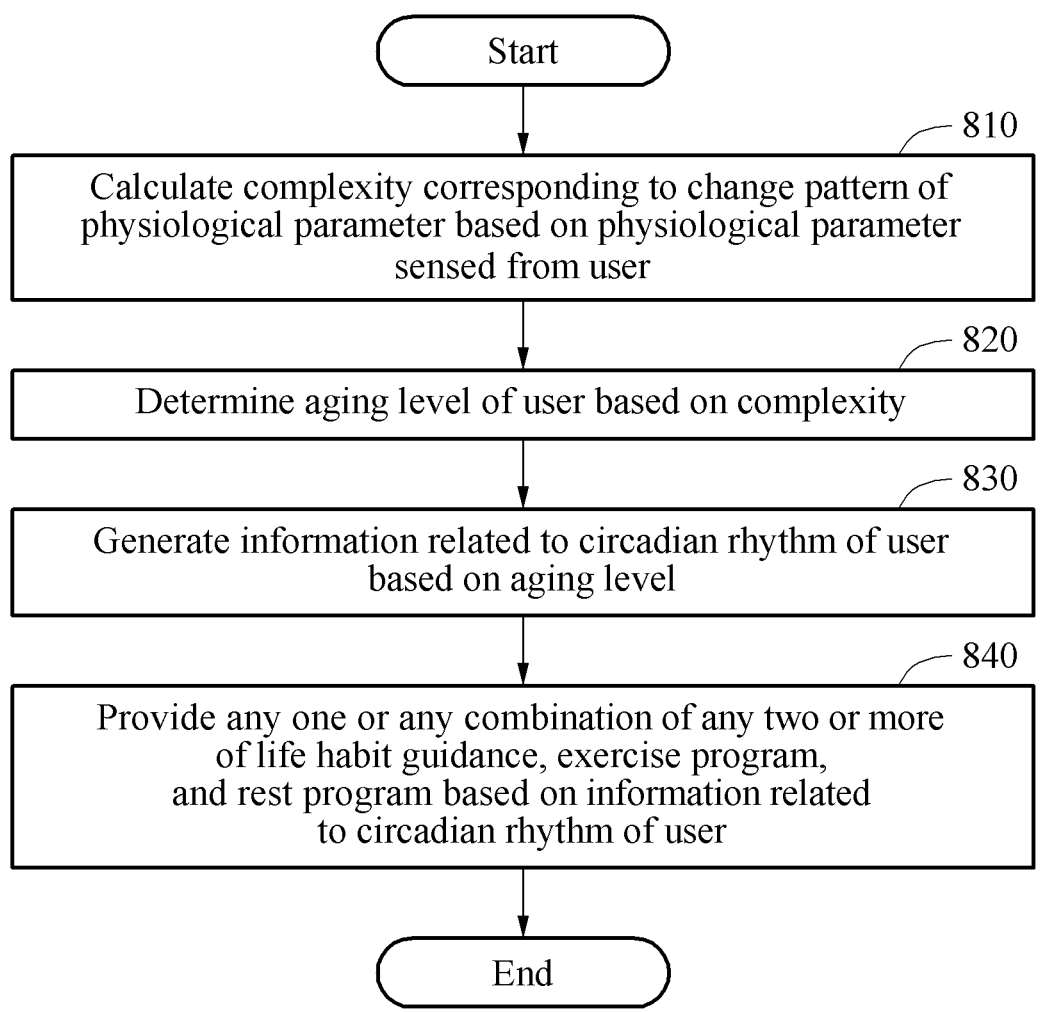
FIG. 8 is a flowchart illustrating an example of another method of evaluating a physiological aging level.

FIG. 8 is a flowchart illustrating an example of another method of evaluating a physiological aging level.

Referring to FIG. 8, an evaluation apparatus calculates a complexity corresponding to a change pattern of a physiological parameter based on the physiological parameter sensed from a user in operation 810. The evaluation apparatus determines an aging level of the user based on the complexity in operation 820.

The evaluation apparatus generates information related to a circadian rhythm of the user based on the aging level in operation 830. As described above, the information related to the circadian rhythm of the user may be construed as including a circadian rhythm of the user, and information indicating the circadian rhythm of the user, for example, a graph or data representing the circadian rhythm. For example, the evaluation apparatus generates information indicating a daily circadian rhythm of the user. A method of generating a graph representing a circadian rhythm of the user using the evaluation apparatus will be described with reference to FIG. 9.

The evaluation apparatus generates cumulative information related to the circadian rhythm by accumulating information related to the circadian rhythm of the user generated during a predetermined time period. For example, the evaluation apparatus generates information indicating a weekly circadian rhythm and a monthly circadian rhythm.

The evaluation apparatus provides any one or any combination of any two or more of a life habit guidance, an exercise program, and a rest program for the user based on the information related to the circadian rhythm of the user and/or the cumulative information related to the circadian rhythm in operation 840.

In one example, evaluation apparatus determine information about times most suitable for sleeping, a mental activity, and an exercise of the user from the information related to the circadian rhythm of the user and/or the cumulative information related to the circadian rhythm. For example, the evaluation apparatus generates life habit guidance information guiding the user to sleep from 10:20 p.m. to 6:00 a.m., perform a mental activity from 8:50 a.m. to 11:30 a.m., and exercise from 8:00 p.m. to 9:00 p.m., and provides the life habit guidance information to the user.

In another example, the evaluation apparatus determines a type of exercise that helps to reduce an aging level of the user among a high-intensity exercise, a moderate-intensity exercise, and a low-intensity exercise from the information related to the circadian rhythm of the user and/or the cumulative information related to the circadian rhythm. For example, the evaluation apparatus determines that performing a moderate-intensity exercise for 40 minutes to one hour between 8:00 p.m. to 9:00 p.m. is most helpful for reducing the aging level of the user. The evaluation apparatus generates an exercise program guiding the user to perform a moderate-intensity exercise for 40 minutes to one hour between 8:00 p.m. to 9:00 p.m., and provides the generated exercise program to the user.

In another example, the evaluation apparatus generates information guiding the user to take a rest every day from 1:00 p.m. to 1:30 p.m., or to take a rest on Saturdays in the morning based on the information related to the circadian rhythm of the user and/or the cumulative information related to the circadian rhythm. The evaluation apparatus provides the rest program for the user based on the information guiding the user to take a rest.

Figure 9:
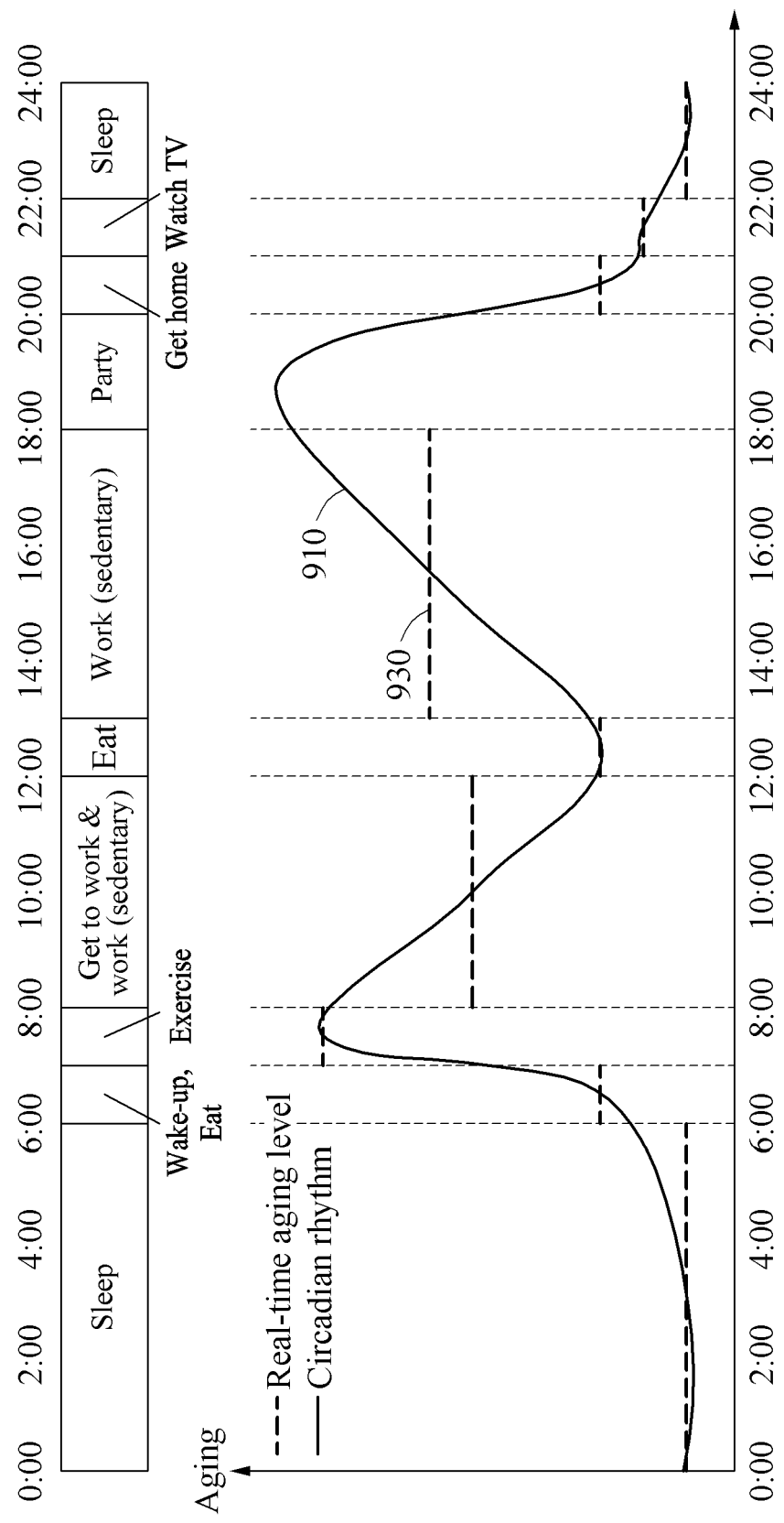
FIG. 9 is a diagram illustrating an example of a method of generating a graph representing a circadian rhythm of a user based on an aging level.

FIG. 9 is a diagram illustrating an example of a method of generating a graph representing a circadian rhythm of a user based on an aging level.

Referring to FIG. 9, a graph 930 representing a daily aging level of a user evaluated in real time based on a physiological parameter continuously sensed from the user during daily life, and a graph 910 representing information related to a circadian rhythm of the user generated based on the daily aging level of the user, for example, the circadian rhythm of the user, are illustrated.

When the aging level of the user for each time slot is determined as shown in the graph 930, an evaluation apparatus generates the graph 910 by interpolating an aging level of the day using, for example, a linear interpolation, a spline interpolation, or an exponential interpolation. In one example, the graph 910 representing a daily circadian rhythm is generated by interpolating a central point of a predetermined time interval in the graph 930 representing the daily aging level of the user. However, the evaluation apparatus may generate a graph representing the circadian rhythm of the user based on daily, weekly, and monthly aging levels using other various methods. For example, in addition to generating a graph representing a daily circadian rhythm using interpolation, the evaluation apparatus may generate a graph representing a daily, weekly, or monthly circadian rhythm by averaging premeasured multiple items of circadian rhythm information. Furthermore, the evaluation apparatus may generate a graph representing a circadian rhythm by synchronization with a time of an event that occurs in daily life, for example, a bedtime, a wake-up time, or other daily event.

Further, the evaluation apparatus may generate cumulative information related to the circadian rhythm by accumulating information related to the circadian rhythm generated for a predetermined time period, and generate a graph of the cumulative information (not shown).

Figure 10:
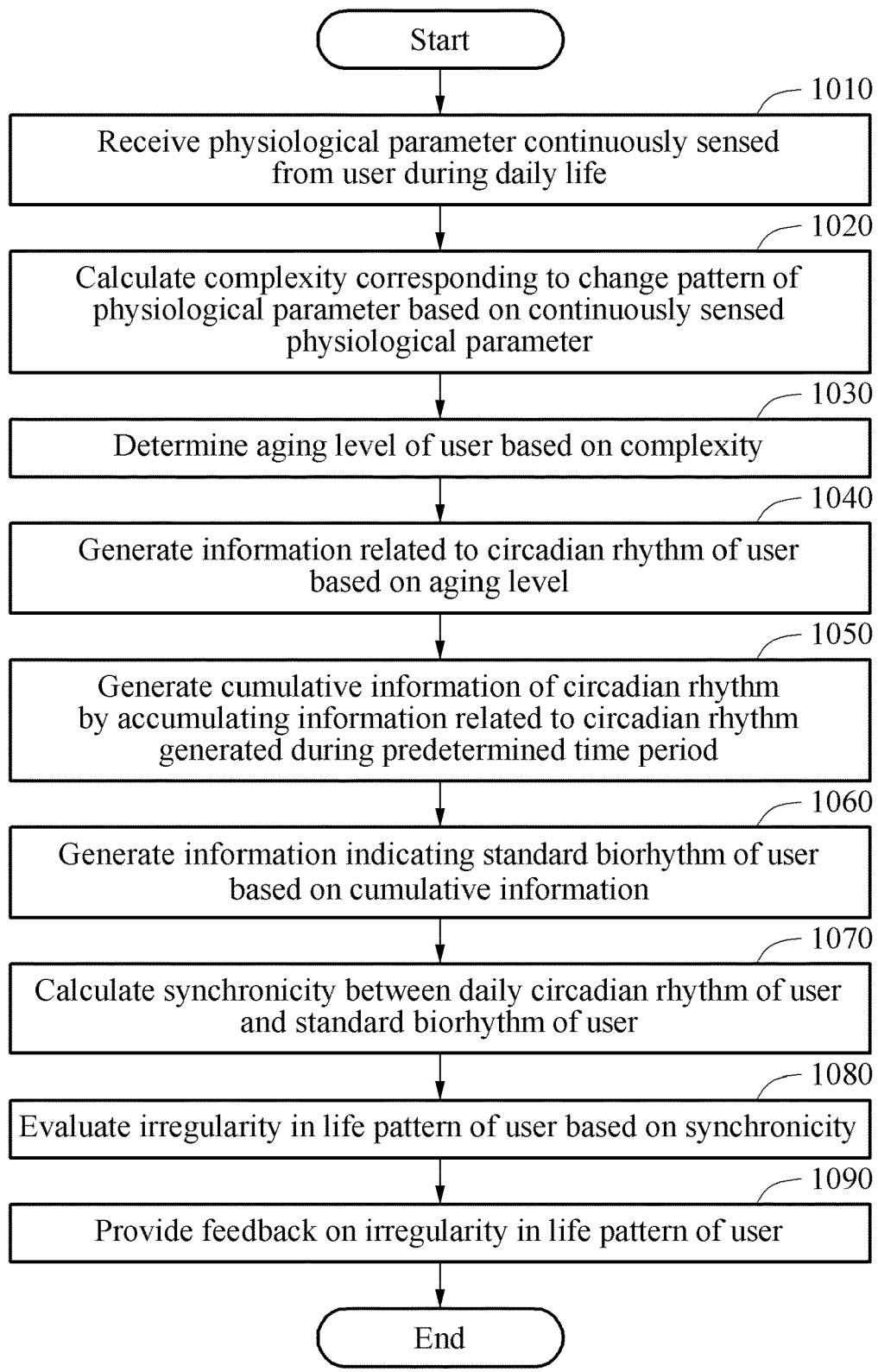
FIG. 10 is a flowchart illustrating another example of a method of evaluating a physiological aging level.

FIG. 10 is a flowchart illustrating another example of a method of evaluating a physiological aging level.

Referring to FIG. 10, an evaluation apparatus receives a physiological parameter continuously sensed from a user during daily life in operation 1010. The evaluation apparatus calculates a complexity corresponding to a change pattern of the physiological parameter based on the continuously sensed physiological parameter in operation 1020. The evaluation apparatus determines an aging level of the user based on the complexity in operation 1030.

The evaluation apparatus generates information related to a circadian rhythm of the user based on the aging level in operation 1040. For example, the evaluation apparatus generates information indicating a daily circadian rhythm of the user.

The evaluation apparatus generates cumulative information related to the circadian rhythm by accumulating the information related to the circadian rhythm generated during a predetermined time period in operation 1050.

The evaluation apparatus generates information indicating a standard biorhythm of the user based on the cumulative information in operation 1060. The evaluation apparatus generates the information indicating the standard biorhythm of the user based on the cumulative information using various interpolations as described above with reference to FIG. 9. The information indicating the standard biorhythm of the user may be construed as including the standard biorhythm of the user, and a graph or list indicating the standard biorhythm.

In one example, the evaluation apparatus generates information for improving a life habit of the user based on the standard biorhythm of the user, and provides the information for improving the life habit to the user.

The evaluation apparatus calculates a synchronicity between the daily circadian rhythm of the user and the standard biorhythm of the user in operation 1070. In this application, synchronicity includes all concepts indicating a correspondence or a similarity, for example, a conformity and a correlation.

The evaluation apparatus evaluates an irregularity in a life pattern of the user based on the synchronicity in operation 1080. The evaluation apparatus provides a feedback on the evaluated irregularity in the life pattern of the user in operation 1090. For example, the irregularity in the life pattern of the user is provided in a form of a graph representing a difference in synchronicity between the daily circadian rhythm and the standard biorhythm of the user. The irregularity in the life pattern of the user is provided in a form of a text message or voice message such as, for example, "Your life pattern today indicates constant overwork compared to your standard biorhythm. Please take a rest later."

In one example, the evaluation apparatus generates information for improving the life habit of the user based on the standard biorhythm of the user, and provides the generated information to the user. When a bedtime or a wake-up time is determined to be excessively late based on the standard biorhythm of the user, the evaluation apparatus generates information guiding the user to sleep within a suitable time range, and provides the generated information to the user.

In another example, the evaluation apparatus predicts a risk of disease, for example, a metabolic syndrome, Alzheimer's disease, diabetes, and hypertension, of the user based on the irregularity in the life pattern of the user evaluated based on the standard biorhythm of the user. The evaluation apparatus calculates a health score of the user based on the risk of disease of the user, and estimates a mortality risk rate based on the health score of the user. For example, the evaluation apparatus displays a sentence of "you are currently at risk of metabolic syndrome" on a display, or provides an audible warning.

In another example, the evaluation apparatus provides a life habit prescription for reducing the risk of metabolic syndrome of the user. In this example, a life habit prescription for reducing a risk of disease is pre-stored in a database. The life habit prescription may be construed as including, for example, an exercise prescription, a nutrition prescription, and a rest prescription. In addition, the evaluation apparatus provides a suitable exercise duration and a suitable exercise intensity to the user based on the standard biorhythm of the user.

The evaluation apparatus 100, the sensor 103, the processor 106, the wearable device 110, the mobile device 130, the wearable device 210, the sensor 213, the wireless module 216, the mobile device 230, the memory 231, the processor 233, the UI 235, the guide provider 237, and the wireless module 241 illustrated in FIGS. 1A, 1B, and 2 that perform the operations described with respect to FIGS. 1A-10 are implemented by hardware components. Examples of hardware components include controllers, sensors, generators, drivers, memories, comparators, arithmetic logic units, adders, subtractors, multipliers, dividers, integrators, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1A-10. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 3, 5, 8, and 10 that perform the operations described herein with respect to FIGS. 1A-10 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A method of evaluating a physiological aging level, the method comprising:
   sensing, by a sensor, a physiological parameter from a user;
   a non-transitory computer-readable storage medium storing instructions executable by a processor; and
   a processor including a neural network or support vector machine executing the instructions to:
   calculate a complexity corresponding to a change pattern of the physiological parameter based on the physiological parameter sensed from the user; and
   determine a first aging level of the user in a first time interval indicating a physiological change progress of the user based on the complexity, and determining an aging level of the user in a second time interval based on the first aging level,
   wherein the calculation of the complexity further comprises calculating a relative ratio of the physiological parameter to the complexity or a relative ratio of a variance in the physiological parameter to the complexity, and
   wherein the determination of the aging level further comprises the application of a linear or non-linear equation by the processor through the neural network or the support vector machine which includes generation of feature vectors from the complexity.

2. The method of claim 1, wherein the calculation of the complexity further comprises:
   calculating a variance in the complexity based on the complexity.

3. The method of claim 2, wherein the determination of the aging level further comprises determining the aging level based on the complexity and either one or both of the variance in the complexity and the relative ratio.

4. The method of claim 1, wherein the determination of the aging level further comprises determining the aging level by substituting the complexity into an aging function.

5. The method of claim 4, wherein the aging function comprises at least one coefficient determined using a regression analysis performed based on the complexity and information related to an age of the user.

6. The method of claim 1, wherein the calculation of the complexity further comprises calculating the complexity of the physiological parameter based on any one or any combination of any two or more of a Poincaré plot of the physiological parameter, a fractal dimension of the physiological parameter, a chaotic dynamic parameter of the physiological parameter, and an entropy of the physiological parameter.

7. The method of claim 1, wherein the calculation of the complexity further comprises calculating a decrease rate of the complexity or an increase rate of the complexity.

8. The method of claim 1, wherein the physiological parameter comprises any one or any combination of any two or more of a heart rate, a blood pressure, and a pulse transit time (PTT) of the user.

9. The method of claim 1, further comprising receiving a physiological parameter continuously sensed from the user during a daily life of the user;
wherein the calculation of the complexity further comprises calculating the complexity based on the physiological parameter continuously sensed from the user.

10. The method of claim 1, wherein the determination of the aging level further comprises evaluating an aging level of the user based on a reference aging level.

11. The method of claim 1, wherein the determination of the aging level further comprises determining the aging level of the user based on preset gender-specific and age-specific aging levels.

12. The method of claim 1, wherein the determination of the aging level further comprises determining the aging level of the user based on a time or a state of the user; and
the state of the user is based on a physical activity of the user.

13. The method of claim 12, further comprising receiving the state of the user from the user.

14. The method of claim 1, further comprising generating information related to a circadian rhythm of the user based on the aging level.

15. The method of claim 14, wherein the generating comprises generating cumulative information related to the circadian rhythm by accumulating information related to the circadian rhythm generated during a predetermined period.

16. The method of claim 15, further comprising generating information indicating a standard biorhythm of the user based on the cumulative information.

17. The method of claim 16, further comprising:
generating information for improving a life habit of the user based on the information indicating the standard biorhythm of the user; and
providing the information for improving the life habit to the user.

18. The method of claim 16, wherein the generating of the information related to the circadian rhythm comprises generating information indicating a daily circadian rhythm of the user.

19. The method of claim 18, further comprising:
calculating a synchronicity between the daily circadian rhythm of the user and the standard biorhythm of the user;
evaluating an irregularity in a life pattern of the user based on the synchronicity; and
providing feedback on the evaluated irregularity to the user.

20. The method of claim 14, further comprising providing any one or any combination of any two or more of a life habit guidance, an exercise program, and a rest program for the user based on the information related to the circadian rhythm of the user.

21. An apparatus for evaluating a physiological aging level, the apparatus comprising:
a sensor configured to sense a physiological parameter from a user; and
a processor configured to calculate a complexity corresponding to a change pattern of the physiological parameter based on the physiological parameter sensed from the user, to determine a first aging level in a first time interval indicating a physiological change progress of the user based on the complexity, and to determine an aging level of the user in a second time interval based on the first aging level,
wherein the processor is further configured to calculate a relative ratio that is a relative ratio of the physiological parameter to the complexity or a relative ratio of the variance in the physiological parameter to the complexity, and to determine the first aging level based on the complexity and the relative ratio.

22. The apparatus of claim 21, wherein the processor is further configured to calculate a variance in the complexity and, and to determine the first aging level based on the complexity and either one or both of the variance in the complexity and the relative ratio.

23. The apparatus of claim 21, wherein the sensor is further configured to continuously sense the physiological parameter from the user during daily life of the user; and
the processor is further configured to calculate the complexity based on the physiological parameter continuously sensed from the user.

24. The apparatus of claim 21, wherein the processor is further configured to evaluate the aging level of the user relative to an actual age of the user or a target age based on a reference aging level corresponding to the actual age of the user or the target age.

25. The apparatus of claim 21, wherein the processor is further configured to determine the aging level of the user based on a time or a state of the user; and
the state of the user is based on a physical activity of the user.

26. The apparatus of claim 25, further comprising a user interface (UI) configured to receive the state of the user from the user.

27. The apparatus of claim 21, wherein the processor is further configured to generate information related to a circadian rhythm of the user based on the aging level.

28. The apparatus of claim 27, wherein the processor is further configured to generate cumulative information by accumulating information related to the circadian rhythm generated during a predetermined period, and generate information indicating a standard biorhythm of the user based on the cumulative information.

29. An apparatus for evaluating an aging characteristic, the apparatus comprising:
a sensor configured to sense a physiological parameter from a user; and
a processor configured to calculate a complexity corresponding to a change pattern of the physiological parameter based on the physiological parameter sensed from the user, and to determine a first aging characteristic of the user in a first time interval based on the complexity, and to determine an aging characteristic of the user in a second time interval based on the first aging characteristic, wherein the processor is further configured to calculate a relative ratio that is a relative ratio of the physiological parameter to the complexity or a relative ratio of the variance in the physiological parameter to the complexity, and to determine the first aging characteristic based on the complexity and the relative ratio.

30. The apparatus of claim 29, wherein the processor is further configured to compare the aging characteristic of the user to a reference aging characteristic, and evaluate the aging characteristic of the user based on a result of the comparing.

31. The apparatus of claim 29, wherein the processor is further configured to calculate a difference between the aging characteristic of the user and a reference aging characteristic, accumulate the difference over a period of time, and evaluate the aging characteristic of the user based on the accumulated difference.

32. The apparatus of claim 31, wherein the aging characteristic of the user is an aging level of the user that changes as a level of physical activity of the user changes and represents a physiological change progress of the user due to aging of the user;

the reference aging characteristic is a reference aging level corresponding to an actual age of the user or a target age; and the processor is further configured to evaluate the aging level of the user as being greater than the reference aging level in response to the accumulated difference being positive, and as being less than the reference aging level in response to the accumulated difference being negative.

* * * * *